US006935340B2

(12) United States Patent
Saied

(10) Patent No.: US 6,935,340 B2
(45) Date of Patent: Aug. 30, 2005

(54) ENDOTRACHEAL INTUBATION ASSISTANCE DEVICE

(76) Inventor: V. C. Saied, 2802 Hamilton Blvd., Wichita Falls, TX (US) 76038

( * ) Notice: Subject to any disclaimer, the term of this patent is extended or adjusted under 35 U.S.C. 154(b) by 324 days.

(21) Appl. No.: 09/975,178

(22) Filed: Oct. 11, 2001

(65) Prior Publication Data
US 2003/0070684 A1 Apr. 17, 2003

(51) Int. Cl.$^7$ ............................................. A61G 15/00
(52) U.S. Cl. ...................................... 128/845; 128/846
(58) Field of Search ................................ 128/869, 870; 5/636, 640, 644

(56) References Cited

U.S. PATENT DOCUMENTS

| | | | | |
|---|---|---|---|---|
| 3,870,038 | A | * 3/1975 | Arblaster | 128/28 |
| 4,005,498 | A | * 2/1977 | Starr | 5/81 R |
| 4,805,603 | A | * 2/1989 | Cumberland | 128/75 |
| D301,669 | S | 6/1989 | Dwelly | |
| 4,918,774 | A | * 4/1990 | Popitz | 5/441 |
| 5,048,136 | A | * 9/1991 | Popitz | 5/431 |
| 5,184,365 | A | * 2/1993 | Stafford | 5/632 |
| 5,287,577 | A | * 2/1994 | Bremer | 5/644 |
| 5,483,974 | A | * 1/1996 | Crangle | 128/774 |
| 5,528,783 | A | * 6/1996 | Kunz | 5/634 |
| 5,540,231 | A | * 7/1996 | Moy | 128/677 |
| 5,893,183 | A | * 4/1999 | Bechtold | 5/632 |
| 6,038,722 | A | * 3/2000 | Giori | 5/709 |
| 6,065,166 | A | 5/2000 | Sharrock et al. | |
| 6,095,972 | A | 8/2000 | Sakamoto | |
| 6,123,666 | A | 9/2000 | Wrenn et al. | |
| 6,142,144 | A | 11/2000 | Pacey | |
| 6,174,281 | B1 | 1/2001 | Abramowitz | |
| 6,231,505 | B1 | 5/2001 | Martin | |
| 6,327,724 | B1 | 12/2001 | Sharrock et al. | |

OTHER PUBLICATIONS

World Wide Web, http://www.pocketpillow.net/, Pocket–Pillow, Courtesy Service Products, LTD, printed on Sep. 24, 2002, 4 pages.
World Wide Web, http://www.medslant.com/MED–about–1.htm, MEDSLANT, printed on Sep. 23, 2002, 2 pages.
World Wide Web, http://www.hygeco.com/english/00231.htm, Hygeco Inflatable Pillow, Hygeco 2000, printed on Sep. 24, 2002, 1 page.
World Wide Web, http://www.hygeco.com/resource/products/highres/00231.jpg, printed on Sep. 24, 2002, 1 page.
World Wide Web, http://www.comfortchannel.com/prod.itml/icOid/568?source=googleadwords, Sleepmatters Adjustable Air Pillow, printed on Sep. 24, 2002, 2 pages.
World Wide Web, http://www.safetycentral.com/inpilseatcus.html, Inflatable Pillow/Seat Cushion, 2002, printed on Sep. 24, 2002, 2 pages.
Elizabeth Douglas, "Some Hairstyles Can Complicate Intubation," Anesthesiology News, vol. 27 (No. 8), p. 1, 34, (Aug., 2001).

* cited by examiner

Primary Examiner—Michael A. Brown
(74) Attorney, Agent, or Firm—Haynes and Boone, LLP

(57) ABSTRACT

An endotracheal intubation assistance device is disclosed. The device is placed under the head and shoulders of a patient in a supine position. The device comprises a first chamber being inflatable to raise the shoulders of the patient relative to the head of the patient thereby facilitating insertion and proper placement of a laryngoscope blade into the mouth of the patient. The device also comprises a second chamber coupled to the first chamber, the second chamber being inflatable to raise the head of the patient relative to the shoulders of the patient thereby facilitating visualization of the patient's glottis for insertion of an endotracheal tube. The device may also comprise a pressure applicator to apply pressure to a cricoid cartilage of the patient. The pressure applicator may comprise a pressure chamber which may be inflated to apply additional pressure.

47 Claims, 2 Drawing Sheets

ENDOTRACHEAL INTUBATION ASSISTANCE DEVICE

TECHNICAL FIELD OF THE INVENTION

The present invention relates generally to the field of medical devices, and more particularly to an endotracheal intubation assistance device.

BACKGROUND OF THE INVENTION

Laryngoscopes are well known in the art and are used in intubating the trachea for administration of general anesthesia, during emergency situations in resuscitation and for mechanical ventilation. Endotracheal intubation requires the insertion of a flexible tube through the oral cavity (or sometimes nasal cavity), the oropharynx, the glottis and into the trachea. Safe and successful intubation requires controlled insertion of the endotracheal tube so that the tube is introduced through the glottis of the larynx without damaging the teeth or surrounding tissues such as oropharynx, epiglottis, vocal cords or laryngeal cartilages. It is desirable that the practitioner inserting the tube have as clear a view as possible of the glottis and vocal cords to guide the tube into the trachea successfully and without injury to the patient.

Frequently it is difficult or even not possible to obtain a clear view of the glottis, so it is desirable that optimal positioning of the laryngoscope blade and the patient's head be attained for increasing the success of endotracheal intubation.

A laryngoscope has a handle and a blade. The laryngoscope blade is used, when inserted properly, to lift the tongue and frequently lift the head upward to create a clear path through the glottis into the trachea. Laryngoscopes have a light source for illuminating the mouth, oropharynx and glottis to enhance accurate placement of the laryngoscope blade and insertion of the endotracheal tube.

The intubation process typically requires extending the head of the patient to facilitate insertion of the laryngoscope blade into the mouth. With the laryngoscope blade in place against the tongue of the patient, the practitioner uses the laryngoscope to lift the tongue and frequently lift the patient's head with the blade to expose the glottis into view.

There are several problems with the conventional manner in which endotracheal intubation is performed. Because the blade is used to lift and position the patient's head, there is a certain likelihood of trauma to the soft tissues of the patient's mouth, pharynx, vocal cords, laryngeal cartilages and to the teeth, leading to bleeding, sore throat, hoarseness or dislodgment or breakage of teeth. Although some endotracheal intubations are simple and require little raising and manipulation of the head, even in routine non-difficult intubations, some blood is frequently noted on removal of the endotracheal tube indicating a degree of trauma to the patient's tissues.

Furthermore, because the practitioner typically uses his/her weaker non-dominant hand to hold the laryngoscope handle and insert the laryngoscope blade so that the dominant hand can be used to insert the endotracheal tube, the practitioner often has difficulty lifting, supporting and manipulating the patient's head, particularly a very heavy head, with the weaker non-dominant arm and hand. This is particularly a problem in practitioners with weaker arms and hands. Therefore, in a substantial percentage of cases, the practitioner is required to request and wait for another person's, typically a nurse's, assistance in lifting the patient's head into optimal position. This person also frequently is asked to apply pressure on the front part of the neck over the cricoid cartilage for better visualization of the glottis and to prevent aspiration of gastric contents which can cause pneumonia, lung abscesses or even death. The necessity of calling for and requiring an assistant causes delay and interferes with the nurse's performance of his/her tasks in getting the surgical procedure underway.

When an endotracheal intubation cannot be accomplished with just the use of a laryngoscope, other methods such as those using special laryngoscopic equipment and/or intubating bronchoscopes must be used. However, the use of these other methods requires additional time, thereby delaying the initiation of the surgical, diagnostic or medical procedure, increasing the possibility of causing hypoxia to the patient and increasing the patient's cost.

SUMMARY OF THE INVENTION

Accordingly, there is a desire for a device to assist in the endotracheal intubation process, for example a device that aids in the placement and support of the patient's head in an optimal position for endotracheal intubation.

In accordance with an embodiment of the present invention, an endotracheal intubation assistance device is disclosed. The endotracheal intubation assistance device is placed under the head and upper shoulders of the patient in a supine position. A first chamber of the device is inflated to raise the patient's shoulders which tilts the head back tending to open the mouth to facilitate insertion of the laryngoscope blade into the patient's mouth. The first chamber is substantially deflated after insertion of the laryngoscope blade into the patient's mouth. A second chamber of the device is inflated to raise the head of the patient to facilitate viewing the patient's glottis for insertion of the endotracheal tube.

The endotracheal intubation assistance device may include a pressure applicator comprising a strap to apply pressure to the patient's cricoid cartilage when the patient's head is raised due to inflation of the second chamber. The pressure applicator may also include an inflatable pressure chamber to apply additional pressure to the patient's cricoid cartilage. This helps provide better visualization of the glottis, particularly in patients with an anatomically anterior situated larynx, and it protects against aspiration of gastric contents.

In accordance with another embodiment of the present invention, the endotracheal intubation assistance device comprises a mechanical system to independently raise and lower the shoulders and head of the patient.

Other aspects of the invention will become apparent to those skilled in the art upon review of the following description of specific embodiments of the invention in conjunction with the accompanying figures.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

Figure 1:
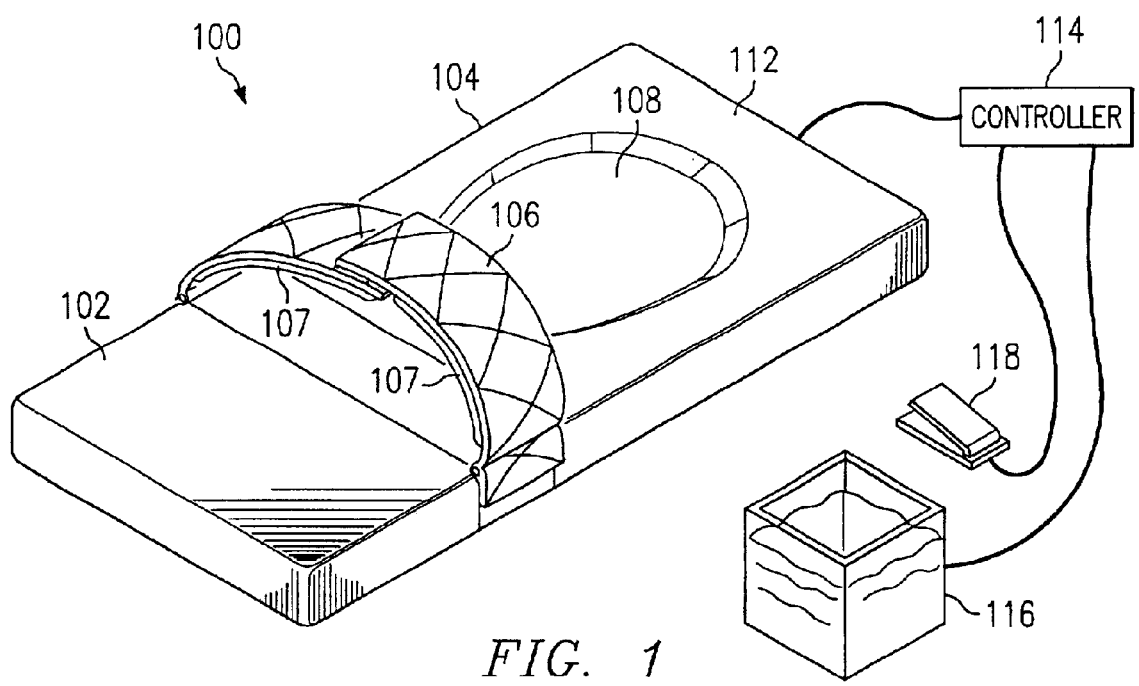
FIG. 1 is an isometric view of an endotracheal intubation assistance device according to a preferred embodiment of the present invention.

The preferred embodiment of the present invention and its advantages are best understood by referring to FIGS. 1 and 2 of the drawings.

FIG. 1 is an isometric view of an endotracheal intubation assistance device 100 according to a preferred embodiment of the present invention. Intubation assistance device 100 is preferably a pillow, cushion, or support that has at least two independently adjustable chamber—a first chamber 102 and a second chamber 104. First chamber 102 and second chamber 104 are preferably coupled to each other to form an integral unit.

First chamber 102 of endotracheal intubation assistance device 100 is used to support the shoulder regions of a person, for example a patient to be intubated, and second chamber 104 is used to support the head of the patient. Second chamber 104 preferably includes a concave depression 108 on at least its upper surface 112 for "cupping" and providing stability to the head of the patient. Each of the two chambers is preferably air tight with gas-impermeable walls so that it is capable of being independently inflated and deflated. Inflation and deflation of the individual chambers 102 and 104 facilitates raising and lowering of the patient's head and shoulders supported by the respective chambers. If desired, chambers 102 and 104 may be independently manipulated or operated so as to raise and lower the head and shoulders of the patient. Although intubation assistance device 100 as shown in FIG. 1 is rectangular in shape the invention is not so limited and in alternative embodiments, intubation assistance device 100 may be of any shape.

If desired, intubation assistance device 100 may also include a pressure applicator 106. Pressure applicator 106 comprises a strap with an adjustable length. Pressure applicator 106 may include an inflatable elongated chamber 107 disposed along an inner surface of the strap. Pressure applicator 106 may be coupled to intubation assistance device 100 preferably close to the boundary of the two chambers 102 and 104 and may be adjusted to extend across upper surface 112 of intubation assistance device 100 around the neck of a patient. Pressure applicator 106 is used to apply pressure to a specific spot of the patient's neck when the neck is in a particular position as discussed herein below. Chamber 107 may be inflated to apply additional pressure, if necessary.

The inflation/deflation of chambers 102, 104 and 107 of intubation assistance device 100 may be controlled by a controller 114. In the preferred embodiment, controller 114 does not require the practitioner to use his/her hands for operating intubation assistance device 100 as it is desirable that the practitioner use his/her non-dominant hand to insert the laryngoscope and use the dominant hand to insert the endotracheal tube, into the patient's mouth. Thus, controller 114 may receive input from an actuating device 118, such as a foot pedal. If desired, controller 114 may be voice activated to follow the practitioner's verbal commands to inflate and deflate chambers 102, 104 and 107. Alternatively, controller 114 may be hand operated with actuating device 118 in proximity to the patient's head. In another alternative embodiment, actuating device 118, which is preferably a foot pedal, may be coupled to a bellows (not shown). By applying pressure on the foot pedal, air from the bellows may be used to inflate chambers 102, 104 and 107. The different chambers 102, 104 and 107 may be deflated by removing pressure from the foot pedal.

The different chambers 102, 104 and 107 of intubation assistance device 100 may be adapted to couple to a supply of inflatant 116 and a pump (not shown) under the control of controller 114 to inflate the different chambers 102, 104 and 107. The inflatant may be air, nitrogen or any other suitable gases or liquids. One or more of chambers 102, 104 and 107 may comprise a self expanding foam having a gas-impermeable outer barrier and an inner foam cell structure which may be deflated by evacuating air from the cells therein. Deflation of the foam causes deflation of the chamber. Upon releasing the suction, the foam expands with incoming ambient air and returns to its original size. Inflatant supply 116 may comprise a tank located in the operating room itself or a central supply. Preferably, each of the chambers 102, 104 and 107 is individually coupled to inflatant supply 116 to allow each chamber to be independently inflated and deflated. Thus, for example the practitioner may inflate first chamber 102 to a desired degree to facilitate insertion of the laryngoscope blade into the mouth of the patient. The practitioner may deflate first chamber 102 and inflate second chamber 104 to a different degree to raise the head of the patient to facilitate viewing the glottis of the patient for insertion of an endotracheal tube. Chamber 107 may be inflated independently of or with inflation of second chamber 104. One or more outlet valves (not shown) may be provided to allow each chamber to be independently deflated.

Intubation assistance device 100 is preferably a portable device separate from an operating table. However, if desired, it may be incorporated in a headrest of the operating table, a stretcher, a gurney and other apparatus.

Figure 2A:
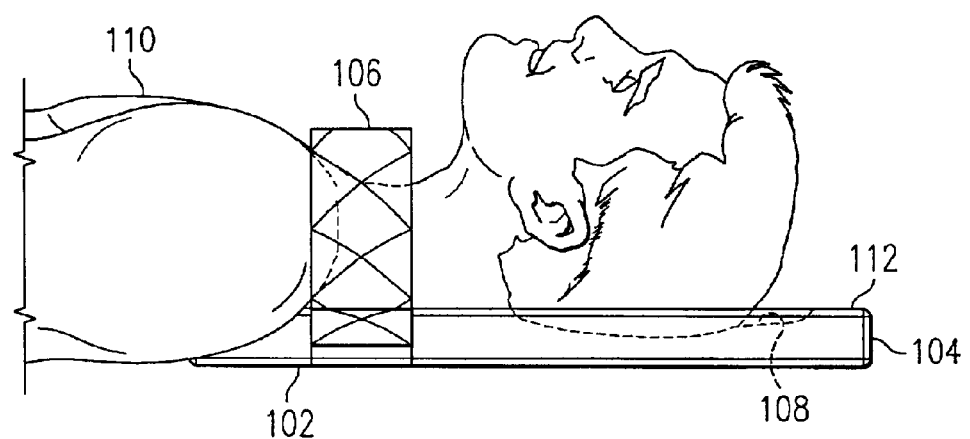
FIGS. 2A–2D illustrate the sequential operation of the endotracheal intubation assistance device of FIG. 1 according to a preferred embodiment of the present invention.

FIGS. 2A–2D illustrate the sequential operation of endotracheal intubation assistance device 100 according to a preferred embodiment of the present invention. In FIG. 2A, a patient 110 to be intubated is shown lying in a supine position with his head supported on upper surface 112 of intubation assistance device 100. The head of patient 110 rests in depression 108 of second chamber 104. Intubation assistance device 100 as shown in FIG. 2A is deflated or in its initial operating mode. If desired, intubation assistance device 100 may be used as a pillow for the head of patient 110 with second chamber 104 being partially inflated for the patient's comfort. If desired, first chamber 102 may be initially inflated to elevate the shoulders of patients who have tightly woven and firmly attached hairpieces to the occipital portion of the head. With the patient in the supine position, it is extremely difficult to insert the laryngoscope blade into the mouth unless the shoulders are elevated. Pressure applicator 106 is shown loosely fastened around the patient's neck, but need not be fastened at this point.

Figure 2B:
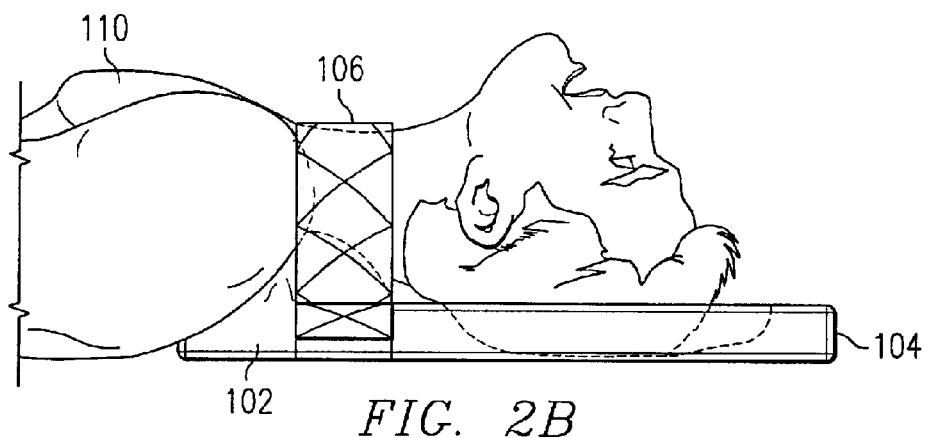

In FIG. 2B, the practitioner has raised first chamber 102 to elevate the shoulders of patient 110. First chamber 102 may be raised by inflating the chamber. In this position, the patient's head is extended and tilted back with the chin elevated tending to open the patient's mouth. Once the shoulders of the patient have been raised and the head extended, a laryngoscope blade may be more conveniently inserted into the mouth of the patient for the purpose of holding the patient's mouth open and displacing the patient's tongue. First chamber 102 may be inflated to a predetermined height or a height adjustable by the practitioner.

Figure 2C:
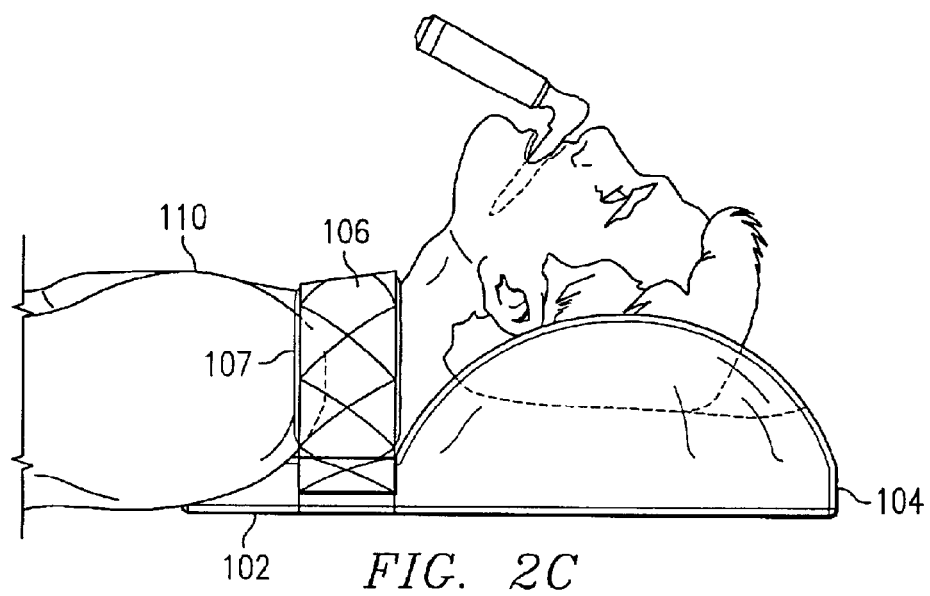

In FIG. 2C, second chamber 104 is in a raised position while first chamber 102 is in a lowered position. Second chamber 104 may be raised by inflating the chamber. First chamber 102 may be lowered by deflating the chamber. The inflation of second chamber 104 causes the head of the patient to be raised. Second chamber 104 may be inflated to a predetermined height or a height adjustable by the practitioner. By adjusting the amount of inflation of second chamber 104, the head of the patient is raised to a desired "sniffing" position to facilitate viewing the glottis of the patient for endotracheal intubation. At the same time, pressure applicator 106, fastened properly around the patient's neck, applies pressure to the cricoid cartilage of the neck. In this manner, pressure is applied to the cricoid and against the esophagus thereby preventing stomach contents of the patient from entering the pharynx and lungs. Applying pressure to the cricoid cartilage also facilitates visualization of the glottis and is particularly useful in patients with an anatomically anterior situated larynx. Chamber 107 may be inflated or deflated to adjust the pressure applied to the cricoid cartilage. Thus, aspiration of the gastric contents into the lungs of the patient is avoided. Inadvertent aspiration of gastric contents may cause pneumonia, lung abscesses or even death of the patient. Pressure applicator 106 may be properly fastened around the patient's neck at any point prior to insertion of the endotracheal tube into the patient's mouth, for example when intubation assistance device 100 is in its initial operating mode as shown in FIG. 2A. Thus, by utilizing intubation assistance device 100, the head of the patient may be oriented and raised to a desired position thereby making it easier and safer for the practitioner to intubate the trachea. Once the patient's head is in the desired position, the endotracheal tube may be inserted into the patient's mouth and placed in the proper position in the trachea.

Figure 2D:
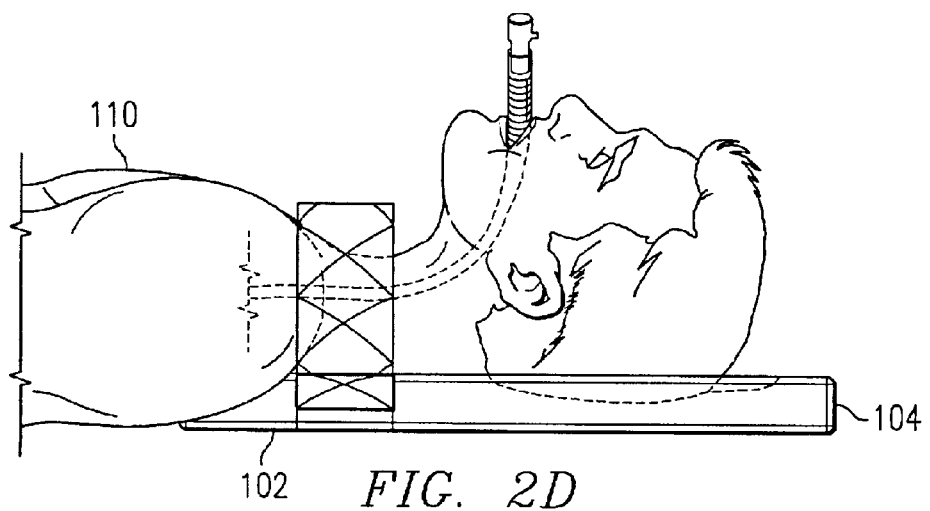

As shown in FIG. 2D, once the laryngoscope and the endotracheal tube are in the desired position, chamber 107 may be deflated and chambers 102 and 104 of intubation assistance device 100 may be lowered to put the patient's head in a normal position. Chambers 102 and 104 may be lowered by deflating chambers 102 and 104.

By using intubation assistance device 100, it is easier for the practitioner to intubate the patient as the practitioner does not have to use the force of the laryngoscope blade alone in order to lift and manipulate the head of the patient to the desired position. Therefore, the number of incidents of trauma and injury to the patient is significantly lowered. Furthermore, the delay associated with waiting for another person to provide assistance is avoided. Moreover, because the intubation assistance device of the present invention is intended to assist the practitioner in intubating a patient, the need for an assistant to perform this function is reduced or completely eliminated.

Although in the preferred embodiment, chambers 102 and 104 are raised and lowered by inflating and deflating the chambers, the invention is not so limited. In alternative embodiments, a mechanical system may be provided to raise and lower the chambers. For example, the two chambers may be supported on separate platforms (not shown). In such an embodiment, each of the platforms may be raised or lowered independently of the other platform. Thus, the two chambers 102 and 104 may be raised or lowered independently of each other.

The preferred embodiment endotracheal intubation assistance device aids in placement and support of the patient's head in an optimal position for endotracheal intubation without undue trauma to the patient's tissues and teeth that may otherwise result due to dependence on the laryngoscope blade alone to accomplish the desired head positioning. Furthermore, the need for another person's assistance is avoided. The preferred embodiment endotracheal intubation assistance device increases the probability of successful intubation without the use of specialized intubating equipment, such as special laryngoscopic equipment and/or intubating bronchoscopes.

While the invention has been particularly shown and described by the foregoing detailed description, it will be understood by those skilled in the art that various other changes in form and detail may be made without departing from the spirit and scope of the invention.

What is claimed is:

1. An endotracheal intubation assistance device placed under the head and shoulders of a patient in a supine position, the device comprising:
    a first chamber being inflatable to raise the shoulders of the patient relative to the head of the patient thereby facilitating insertion and proper placement of a laryngoscope blade into the mouth of the patient;
    a second chamber coupled to the first chamber, the second chamber being inflatable to raise the head of the patient relative to the shoulders of the patient hereby facilitating visualization of the patient's glottis for insertion of an endotracheal tube; and
    a pressure applicator coupled to one of said first and second chambers near a boundary of said first and second chambers and operable to apply pressure to a cricoid cartilage of said patient to prevent aspiration of gastric contents into the lungs of the patient and to provide better visualization of a larynx of said patient.

2. The endotracheal intubation assistance device of claim 1, each of said first chamber and said second chamber being operable to couple to a supply of an inflatant.

3. The endotracheal intubation assistance device of claim 2, wherein said inflatant is selected from the group consisting of a gas and a liquid.

4. The endotracheal intubation assistance device of claim 1, wherein at least one of said first and second chambers comprises a self expanding foam.

5. The endotracheal intubation assistance device of claim 4, said at least one of said first and second chambers comprising said self expanding foam being operable to couple to a suction device.

6. The endotracheal intubation assistance device of claim 5, said suction device being operable to remove air from said self expanding foam thereby causing said at least one chamber to deflate.

7. The endotracheal intubation assistance device of claim 1, said first and said second chambers being inflatable independently of one another.

8. The endotracheal intubation assistance device of claim 7, further comprising a controller operable to control the inflation of said first and second chambers.

9. The endotracheal intubation assistance device of claim 8, further comprising a foot pedal coupled to said controller.

10. The endotracheal intubation assistance device of claim 8, wherein said controller is voice activated.

11. The endotracheal intubation assistance device of claim 8, wherein said controller is hand operated.

12. The endotracheal intubation assistance device of claim 1, said first and said second chambers being deflatable independently of one another.

13. The endotracheal intubation assistance device of claim 7, further. comprising:
    a bellows operable to control inflation and deflation of said first and second chambers; and
    a foot pedal coupled to said bellows and operable to control said bellows.

14. The endotracheal intubation assistance device of claim 1, wherein said pressure applicator comprises an adjustable strap.

15. The endotracheal intubation assistance device of claim 1, wherein said pressure applicator comprises a pressure chamber, said pressure chamber being inflatable independently of said first and second chambers.

16. The endotracheal intubation assistance device of claim 15, said pressure chamber being deflatable independently of said first and second chambers.

17. The endotracheal intubation assistance device of claim 15, wherein said pressure applicator is operable to apply pressure to the cricoid cartilage when said second chamber of said intubation assistance device is inflated, said pressure chamber being inflatable to apply additional pressure to the cricoid cartilage.

18. The endotracheal intubation assistance device of claim 1, wherein said pressure applicator is operable to apply pressure to the cricoid cartilage when said second chamber of said intubation assistance device is inflated to facilitate visualization of the patient's glottis.

19. A method to facilitate endotracheal intubation of a patient with an endotracheal intubation assistance device placed under the head and shoulders of the patient in a supine position, the method comprising:
   inflating a first chamber of said endotracheal intubation assistance device to raise the shoulders of said patient to facilitate insertion of a laryngoscope blade into the patient's mouth;
   substantially deflating said first chamber of said endotracheal intubation assistance device after the insertion of said laryngoscope blade into the patient's mouth; and
   inflating a second chamber of said endotracheal intubation assistance device to raise the head of said patient to facilitate viewing to the patient's glottis for insertion of endotracheal tube.

20. The method of claim 19, further comprising activating an inflatant supply to provide an inflatant to said first chamber to inflate said first chamber.

21. The method of claim 20, further comprising controlling an amount of said inflatant supplied to said first chamber to raise the patient's shoulders to a desired level.

22. The method of claim 21, wherein controlling an amount of inflatant comprises receiving an actuation signal from a foot pedal.

23. The method of claim 21, wherein controlling an amount of inflatant comprises receiving an actuation signal from a hand operated unit.

24. The method of claim 19, further comprising activating an inflatant supply to provide an inflatant to said second chamber to inflate said second chamber.

25. The method of claim 24, further comprising controlling an amount of said inflatant supplied to said second chamber to raise the patient's head to a desired level.

26. The method of claim 25, wherein controlling an amount of inflatant comprises receiving a verbal command.

27. The method of claim 19, further comprising disabling a suction device to allow a self expanding foam of said first chamber to expand thereby causing inflation of said first chamber.

28. The method of claim 19, further comprising disabling a suction device to allow a self expanding foam of said second chamber to expand thereby causing inflation of said second chamber.

29. The method of claim 19, further comprising applying pressure on a foot pedal coupled to a bellows to supply air from said bellows to said first chamber to inflate said first chamber.

30. The method of claim 29, further comprising removing pressure from said foot pedal to deflate said first chamber.

31. The method of claim 30, further comprising applying pressure on said foot pedal to supply air from said bellows to said second chamber to inflate said second chamber.

32. The method of claim 31, further comprising removing pressure from said foot pedal to deflate said second chamber.

33. The method of claim 19, further comprising:
   inserting an endotracheal tube into said patient's trachea; and
   substantially deflating said second chamber of said endotracheal intubation assistance device.

34. The method of claim 19, wherein said inflating of said second chamber occurs substantially simultaneously with said deflating of said first chamber.

35. The method of claim 19, further comprising applying pressure to a cricoid cartilage of said patient to prevent aspiration of gastric contents into the lungs of the patient and to provide better visualization of a larynx of said patient.

36. The method of claim 35, further comprising inflating a pressure chamber of a pressure applicator coupled to one of said first and second chambers to apply additional pressure to said cricoid cartilage.

37. The method of claim 36, further comprising disabling a suction device to allow a self expanding foam of said pressure chamber to expand thereby causing inflation of said pressure chamber.

38. The method of claim 36, further comprising activating an inflatant supply to provide an inflatant to said pressure chamber to inflate said pressure chamber.

39. The method of claim 38, further comprising controlling an amount of said inflatant supplied to said pressure chamber to apply a desired pressure to said cricoid cartilage.

40. An endotracheal intubation assistance device placed under the head and shoulders of a patient in a supine position, the device comprising:
   first and second independently inflatable and deflatable chambers;
   said first chamber being substantially inflated and said second chamber being substantially deflated to raise the shoulders of the patient relative to the head of the patient thereby facilitating insertion of a laryngoscope blade into the mouth of the patient;
   said second chamber being substantially inflated and said first chamber being substantially deflated to raise the head of the patient relative to the shoulders of the patient thereby facilitating visualization of a glottis of the patient for insertion of an endotracheal tube; and
   a pressure applicator coupled to one of said first and second chambers and operable to apply pressure to a cricoid cartilage of said patient.

41. The endotracheal intubation assistance device of claim 40, said pressure applicator comprising a pressure chamber being inflatable and deflatable independently of said first and second chambers.

42. A method to facilitate endotracheal intubation of a patient with an endotracheal intubation assistance device placed under the head and shoulders of the patient in a supine position, the method comprising:
   raising a first section of said endotracheal intubation assistance device to raise the patient's shoulders to facilitate insertion of a laryngoscope blade into the patient's mouth;
   substantially lowering said first section of said endotracheal intubation assistance device after the insertion of said laryngoscope blade into the patient's mouth; and
   raising a second section of said endotracheal intubation assistance device to raise the patient's head to facilitate viewing of the patient's glottis for insertion of an endotracheal tube.

43. The method of claim 42, further comprising supporting said first and second sections on first and second platforms respectively, said first and second platforms being operable to be raised or lowered independently of each other.

44. The method of claim 43, wherein raising said first section comprises raising said first platform supporting said first section.

45. The method of claim 43, wherein raising said second section comprises raising said second platform supporting said second section.

46. An endotracheal intubation assistance device placed under the head and shoulders of a patient in a supine position, the device comprising:

a first section;

a second section coupled to said first section;

a first platform supporting said first section;

a second platform supporting said second section;

said first platform being substantially raised and said second platform being substantially lowered to raise the patient's shoulder relative to the patient's head thereby facilitating insertion of a laryngoscope blade into the mouth of the patient;

said second platform being substantially raised and said first platform being substantially lowered to raise the patient's head relative to the patient's shoulders thereby facilitating visualization of the patient's glottis for insertion of an endotracheal tube; and a pressure applicator coupled to one of said first and second platforms and operable to apply pressure to a cricoid cartilage of said patient.

47. The endotracheal intubation assistance device of claim 46, said pressure applicator comprising a pressure chamber being inflatable and deflatable.

* * * * *